(12) United States Patent
Graumann et al.

(10) Patent No.: US 8,242,925 B2
(45) Date of Patent: Aug. 14, 2012

(54) ARRANGEMENT AND METHOD FOR POSITIONING OF APPARATUSES

(75) Inventors: Rainer Graumann, Höchstadt (DE); Lars Neuefeind, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 267 days.

(21) Appl. No.: 12/436,979

(22) Filed: May 7, 2009

(65) Prior Publication Data
US 2009/0278702 A1   Nov. 12, 2009

(30) Foreign Application Priority Data
May 9, 2008   (DE) .......................... 10 2008 022 921

(51) Int. Cl.
*G08B 21/00* (2006.01)
*H05C 1/02* (2006.01)

(52) U.S. Cl. .................. 340/686.2; 340/686.3; 378/195; 378/198

(58) Field of Classification Search .... 340/686.1–686.6; 600/424, 426, 427, 429; 606/80, 87, 88; 378/195, 198; 74/1 R
See application file for complete search history.

(56) References Cited

U.S. PATENT DOCUMENTS

| | | | |
|---|---|---|---|
| 6,405,072 B1 * | 6/2002 | Cosman | 600/426 |
| 6,814,490 B1 | 11/2004 | Suhm et al. | |
| 7,950,299 B2 * | 5/2011 | Burgkart | 74/1 R |
| 2001/0034530 A1 | 10/2001 | Malackowski et al. | |
| 2008/0269602 A1 * | 10/2008 | Csavoy et al. | 600/426 |
| 2009/0216067 A1 * | 8/2009 | Lebosse et al. | 600/13 |

* cited by examiner

*Primary Examiner* — Van T. Trieu
(74) *Attorney, Agent, or Firm* — Schiff Hardin LLP

(57) ABSTRACT

In an arrangement and associated method for positioning of apparatuses (in particular of a C-arm), the position and orientation of a C-arm and of a pointer instrument are determined by a navigation system, and an alignment of the C-arm is conducted based on the orientation of the pointer apparatus.

9 Claims, 1 Drawing Sheet

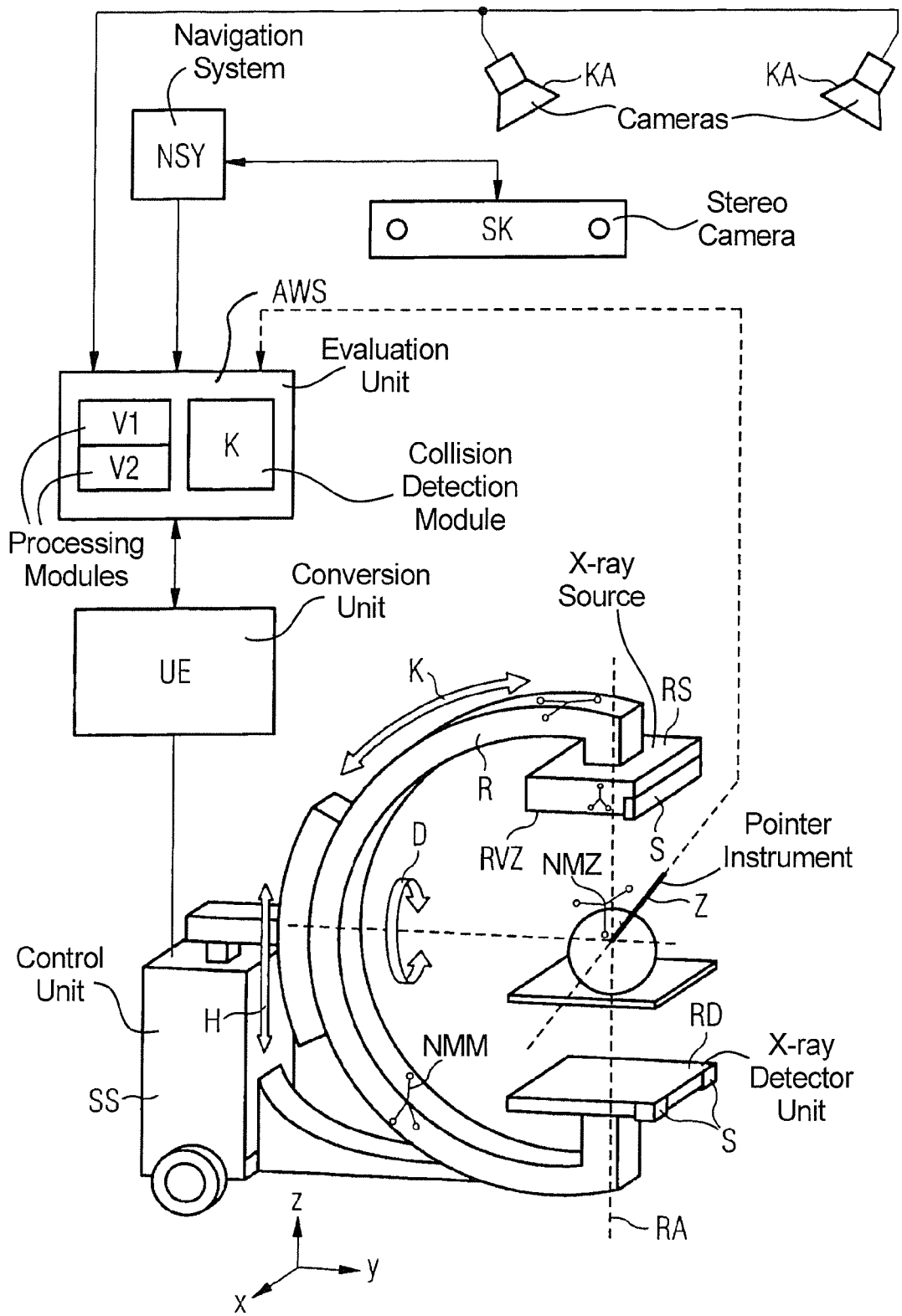

ARRANGEMENT AND METHOD FOR POSITIONING OF APPARATUSES

BACKGROUND OF THE INVENTION

1. Field of the Invention

The present invention concerns a method and apparatus for positioning a component of an apparatus with respect to a designated location.

2. Description of the Prior Art

Among other things, a repeated positioning of apparatuses or apparatus systems at a patient is required before or during a medical operating procedure. During such a procedure, the apparatuses should be positioned outside of the working area of the treating physician or physician team such that these are ready for use at any time. Special precautions are required for use or operation of apparatuses within sterile areas of an operating room in order to achieve sterility. It has previously been typical that apparatuses are moved up to the patients by assistants or by the physician in order to then manually conduct a positioning of the apparatus, such as an x-ray unit. This entails the disadvantage that corresponding apparatus parts must be repeatedly aligned in the same manner on a body part to be examined by the physician or assistants.

SUMMARY OF THE INVENTION

An object of the present invention is to specify an arrangement and an associated method for positioning of apparatuses that avoids or minimizes the above problems.

In the arrangement and the associated method according to the invention, the positions of a pointer instrument provided with at least one first navigation marker, and of an apparatus provided with at least one second navigation marker are detected with a navigation system, and an alignment of the apparatus by, in an evaluation and control unit determining the position and alignment specifications of the pointer instrument and controlling the positioning of the apparatus based thereon.

The invention has the advantage that the treating physician can concentrate on the patient and the subject to be treated.

The invention also has the advantage that a target-oriented alignment of the apparatus can ensue more intuitively.

The invention also provides the advantage that the pointer instrument can be used within sterile areas.

The invention has the advantage that as well as fine positioning of the apparatus are monitored for avoiding collisions.

The invention has the additional advantage that a radiation dose reduction can be achieved due to the simplified, target-oriented positioning and alignment of the x-ray unit.

BRIEF DESCRIPTION OF THE DRAWING

The single FIGURE schematically illustrates an arrangement according to the present invention for positioning an apparatus, which operates according to the inventive method.

DESCRIPTION OF THE PREFERRED EMBODIMENTS

The subject matter of the invention can be applied to any type of apparatus systems. For example, the apparatus system can be stationary and movable apparatus parts of the apparatus system that are to be aligned.

In this arrangement and the associated method for positioning of apparatuses (in particular of a C-arm in an imaging system), the position and alignment of a C-arm and a pointer instrument are determined by a navigation system, and alignment of the C-arm is conducted based on the alignment of the pointer apparatus.

The subsequent exemplary embodiment refers by way of example to a mobile apparatus, in particular a C-arm imaging system. In this arrangement and the associated method, a positioning of the apparatus R and/or of an apparatus unit ensues via a pointer instrument (which can also be designated as a pointer). These apparatuses can be an ultrasound apparatus, a kidney stone disintegration apparatus or a robot-assisted positioning system, for example. The arrangement has (among other things) a pointer instrument Z, a navigation system NSY, an evaluation unit AWS, a conversion unit UE and an x-ray apparatus R with a control unit SS. The pointer instrument Z is fashioned to have at least one navigation marker NMZ. A selection among a number of apparatus units can be made via the pointer instrument Z by differently activating the marker NMZ for different apparatuses. The activation can ensue via control functions that, for example, produce a raising, lowering, rotation or inclination along the degrees of freedom H, K, D of the C-arm. After the evaluation, actuation can occur via the control unit SS with servo-motors associated with the C-arm, and an x-ray unit (formed from an x-ray source RS and an x-ray detector unit RD) can be positioned exactly at the patient. A signal conversion unit UE for voltage level matching between the evaluation unit AWS and control unit SS is provided between the evaluation unit AWS and the apparatus units to be aligned. The pointer instrument Z is provided with a first navigation marker NMZ. A positioning of the apparatus R can be conducted based on a coordinate system X, Y, Z associated with the pointer instrument Z. The direction of the pointer instrument Z is registered by a proximal navigation system NSY equipped with at least one stereo camera SK, for example. The C-arm is likewise provided with at least one second navigation marker NMM by means of which the position of the C-arm and the alignment of the x-ray source RS and the x-ray detector unit RD can be registered. The alignment of the pointer instrument Z and the alignment of the C-arm can be determined with the navigation system NSY using the first and second navigation markers NMZ, NMM. The evaluation unit AWS determines the alignment of the pointer instrument Z in a first processing module V1. The alignment of the pointer instrument Z is reflected by means of a determined direction vector RVZ. Via the arrangement and alignment, in particular of the connecting axis RA between the x-ray unit RS and a detector unit RD of the C-arm that corresponds to this, said C-arm is set in relation to the direction vector RVZ of the pointer instrument Z in a second processing module V2 and is correspondingly aligned.

In a first approach, the x-ray unit R is moved up to the subject O to be imaged. This can ensue manually or mechanically. In both cases, collision monitoring is activated so a collision with other persons or objects can be avoided by signaling and/or by a blocking of the mobile chassis accommodating the C-arm. The transport of the C-arm and the movement of the C-arm (running in defined paths along the degrees of freedom D, H, K) are monitored in the collision detection module K. The signals from sensors S attached to the C-arm (in particular at the outer edges of the x-ray source RS and of the x-ray detector RD) are relayed to this collision detection module K. If a critical distance is reached and the C-arm is still on a collision course, the movement of the C-arm is stopped.

A camera system KA with object detection algorithms can optionally be provided for collision monitoring in the collision detection module K. Object are detected in the collision detection module K, their movement direction is determined and possible collision points are avoided. Upon falling below a predeterminable allowable convergence, the steering of objects movable in the movement path is restricted. This intervention can ensue by the release of a dead man's switch.

If the x-ray unit R is positioned in immediate proximity to the pointer instrument Z, an automatic convergence of the x-ray axis RA with the direction vector VRZ (predetermined by the pointer instrument Z) ensues. An alignment of the x-ray axis RA according to the direction vector RVZ predetermined by the pointer instrument Z continuously ensues in an iterative process.

If the x-ray unit R has taken up the acquisition position optimized for the corresponding x-ray detector unit RD for x-ray acquisition, the x-ray radiation can be triggered by means of a foot switch or trigger unit from an adjoining space.

For example, if the operator requires a C-arm to create an x-ray image, the operator operates the pointer instrument Z located in the workspace and with this point in the direction of C-arm R. The navigation marker NMZ arranged at the pointer apparatus Z is continuously acquired by the stereo camera SK. In the navigation system NSY the position and alignment of the pointer instrument Z and the alignment of the apparatus R is registered and evaluated in the processing units V1, V2. If the pointer instrument Z is directed toward the apparatus R, a virtual contact point of the direction vector is associated with the designated apparatus R. The apparatus R can thereby be set into motion in order to arrive at the operating table, for example. The movement course is additionally monitored by a camera system KA and is stopped if a collision course appears. The pointer instrument Z can likewise be used as such without electronics. A covering of the pointer instrument would be done away with in this case. The trigger pulses to align the x-ray axis RA on the direction vector RVZ of the pointer instrument Z can be triggered and emitted by operating a foot switch. If a number of apparatuses are to be controlled, the electronic evaluation and control unit AE respectively decides to which of these the pointer instrument Z is directed toward using the position and direction information. The alignment and position of the pointer instrument (pointer) Z in space provides the direction and position from which the x-ray acquisition should ensue. The essential coordinates of the x-ray acquisition are therefore established. The movement axis of the C-arm is therefore directly correlated with the movement of the pointer. The distance of the x-ray acquisition system from the patient can additionally be established.

In this embodiment the position and alignment of the pointer Z must be determined only in relation to the coordinate system of the C-arm; this can occur as follows:

As described above, the position and alignment of the pointer is determined by means of the navigation system NSY. This can hereby be an optical, electromagnetic, fiber-optical or mechanical system.

The position and evaluation can be determined in relation to the coordinate system of the C-arm. For example, for this the optical or electromagnetic system can be directly connected with the C-arm. For example, a field generator of an electromagnetic system is located directly integrated into the C-arm (or, alternatively, in the pointer).

Alternatively, the position or the alignment of the pointer can also be determined relative to the C-arm via acceleration sensors in the pointer.

One embodiment is also to determine the position and alignment of the pointer via a wired optical fiber system.

An additional alternative embodiment is a mechanical coupling of the pointer to the C-arm, for example via measurement of axis movements.

If a positioning of the C-arm is determined not only using the patient geometry but also using present image data, the implementation of a registration procedure is then required and the position of the pointer will be determined relative to a fixed coordinate system; for example, the coordinates of an external optical navigation system (for instance for surgical navigation) consisting of navigation system, image data and patient data. The user then directs the pointer using the trajectory planned on the image data.

Although modifications and changes may be suggested by those skilled in the art, it is the intention of the inventors to embody within the patent warranted hereon all changes and modifications as reasonably and properly come within the scope of their contribution to the art.

We claim as our invention:

1. An arrangement for positioning at least one controllable apparatus component in a system, comprising:
   a pointer instrument comprising a first navigation marker;
   an x-ray apparatus comprising positionable x-ray apparatus component to be positioned in space, said x-ray apparatus component comprising a second navigation marker;
   a navigation system that detects and tracks respective positions and orientations of each of said first navigation marker and said second navigation marker;
   said pointer instrument being manually manipulable to orient the pointer instrument relative to a location to which said x-ray apparatus component is to be aligned;
   an evaluation and control unit, connected to said navigation system, configured to identify relative positions and orientations of said pointer instrument and said x-ray apparatus component from the respective detected positions of said first and second navigation markers and to generate position control data in electronic form from the identified relative positions and orientations of the pointer instrument and the apparatus component, and to emit the position control data in electronic form; and
   a positioning device provided with said positioning control data in electronic form operated by said evaluation and control system to position said apparatus component relative to the location designated by said pointer instrument using said positioning control data.

2. An arrangement as claimed in claim 1 wherein said evaluation and control unit comprises a processor configured to identify and evaluate an alignment of said pointer system based on a direction vector having an origin at said pointer instrument.

3. An arrangement as claimed in claim 2 wherein said x-ray apparatus component has an apparatus axis, and wherein said evaluation and control unit is configured to identify an orientation of said pointer instrument and to operate said positioning device to bring said apparatus axis into congruence with the orientation of said pointer instrument.

4. An arrangement as claimed in claim 3 wherein said apparatus component carries a plurality of sensors that respectively emit sensor signals as said apparatus component is being moved by said positioning device, and wherein said evaluation and control unit comprises a collision avoidance module configured to avoid collision of said apparatus component with personnel and other apparatus components of said x-ray apparatus dependent on said sensor outputs.

5. An arrangement as claimed in claim 1 wherein said x-ray apparatus comprises a C-arm forming said x-ray apparatus component, said C-arm having an x-ray source and an x-ray detector mounted thereon.

6. A method for positioning at least one controllable apparatus component in a system, comprising the steps of:

with a navigation system, detecting and tracking respective positions and orientations of each of a first navigation marker carried by a pointer instrument and a second navigation marker on a positionable apparatus to be positioned in space;

manually manipulating said position instrument to orient the pointer instrument relative to a location to which said apparatus component of said x-ray device is to aligned;

in an evaluation and control unit, connected to said navigation system, automatically identifying relative positions and orientations of said pointer instrument and said apparatus component of said x-ray device from the respective detected positions of said first and second navigation markers and generating position control data in electronic form from the identical relative positions and orientations of the pointer instrument and the apparatus component of said x-ray device, and emitting the position control data in electronic form; and providing with said position control data in electronic form from said evaluation and control system, and, with said positioning device, automatically positioning said apparatus component of said x-ray device relative to the location designated by said pointer instrument using said position control data.

7. A method as claimed in claim 6 comprising, in said evaluation and control unit, identifying and evaluating an alignment of said pointer system based on a direction vector having an origin at said pointer instrument.

8. A method as claimed in claim 7 wherein said apparatus component of said x-ray device has an apparatus axis, and comprising, in said evaluation and control unit, identifying an orientation of said pointer instrument and operating said positioning device to bring said apparatus axis into congruence with the orientation of said pointer instrument.

9. A method as claimed in claim 6 wherein said x-ray device comprises a C-arm having an x-ray source and an x-ray detector mounted thereon, and said method comprising attaching said second market to said C-arm, as said positionable apparatus component.

* * * * *